United States Patent
Oosaki et al.

(10) Patent No.: US 8,022,356 B2
(45) Date of Patent: Sep. 20, 2011

(54) SAMPLE AND METHOD FOR EVALUATING RESOLUTION OF SCANNING ELECTRON MICROSCOPE, AND ELECTRON SCANNING MICROSCOPE

(75) Inventors: Mayuka Oosaki, Yokohama (JP); Chie Shishido, Kawasaki (JP); Maki Tanaka, Yokohama (JP); Hiroki Kawada, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 158 days.

(21) Appl. No.: 12/588,517

(22) Filed: Oct. 19, 2009

(65) Prior Publication Data

US 2010/0133426 A1 Jun. 3, 2010

Related U.S. Application Data

(63) Continuation of application No. 11/779,899, filed on Jul. 19, 2007, now Pat. No. 7,605,364.

(30) Foreign Application Priority Data

Sep. 20, 2006 (JP) ................. 2006-253718

(51) Int. Cl.
*G01D 18/00* (2006.01)
*G01N 23/00* (2006.01)
*G21K 7/00* (2006.01)
(52) U.S. Cl. ............ 250/252.1; 250/306; 250/307; 250/310; 250/311
(58) Field of Classification Search ............ 250/252.1, 250/311, 306–307, 310
See application file for complete search history.

(56) References Cited

U.S. PATENT DOCUMENTS

| 5,969,273 | A | 10/1999 | Archie |
| 6,054,710 | A | 4/2000 | Bruggerman |
| 6,080,987 | A | 6/2000 | Belcher |
| 6,449,087 | B2 * | 9/2002 | Ogino ............ 359/383 |
| 6,545,275 | B1 | 4/2003 | Pearl |
| 6,684,686 | B2 * | 2/2004 | Itsuji et al. ......... 73/105 |

(Continued)

FOREIGN PATENT DOCUMENTS

JP 2005-268231 9/2005

OTHER PUBLICATIONS

Joy, et al.; Metrics of resolution and performance for CD-SEMs; In Metrology, Inspection, and Process Control for Microlithography XIV; Proceedings of SPIE 2000; pp. 108-114, vol. 3998.

(Continued)

*Primary Examiner* — David Porta
*Assistant Examiner* — Mindy Vu
(74) *Attorney, Agent, or Firm* — Antonelli, Terry, Stout & Kraus, LLP.

(57) ABSTRACT

A method of evaluating a resolution of a scanning electron microscope includes picking up a first image of a concave and convex pattern formed on a surface of a sample utilizing a first scanning electron microscope, picking up a second image of the concave and convex pattern on the sample utilizing a second scanning electron microscope, respectively processing the first image and the second image in order to evaluate unevenness in resolution between the first scanning electron microscope and the second scanning electron microscope, and determining whether a height of the concave and convex pattern as measured from a bottom thereof is sufficient so that no affection by a secondary electron emitted from the bottom of the concave and convex pattern is exhibited.

10 Claims, 8 Drawing Sheets

U.S. PATENT DOCUMENTS

2005/0133718 A1* 6/2005 Miyamoto et al. ............ 250/307
2006/0011835 A1* 1/2006 Murakoshi et al. ........... 250/310
2006/0043293 A1* 3/2006 Doi et al. ..................... 250/310

OTHER PUBLICATIONS

Archie, et al.; Modeling and Experimental Aspects of Apparent Beam Width as an Edge Resolution Measure; Part of the SPIE Conference on Metrology, Inspection, and Process Control for Microlithography XIII; SPIE Mar. 1999; pp. 669-685; vol. 3677.

Ishitani, et al.; Contrast-to-gradient method for the evaluation of image resolution taking account of random noise in scanning electron microscopy; Japanese Electron of Microscopy; Mar. 31, 2004; pp. 245-255; vol. 53, No. 3.

* cited by examiner

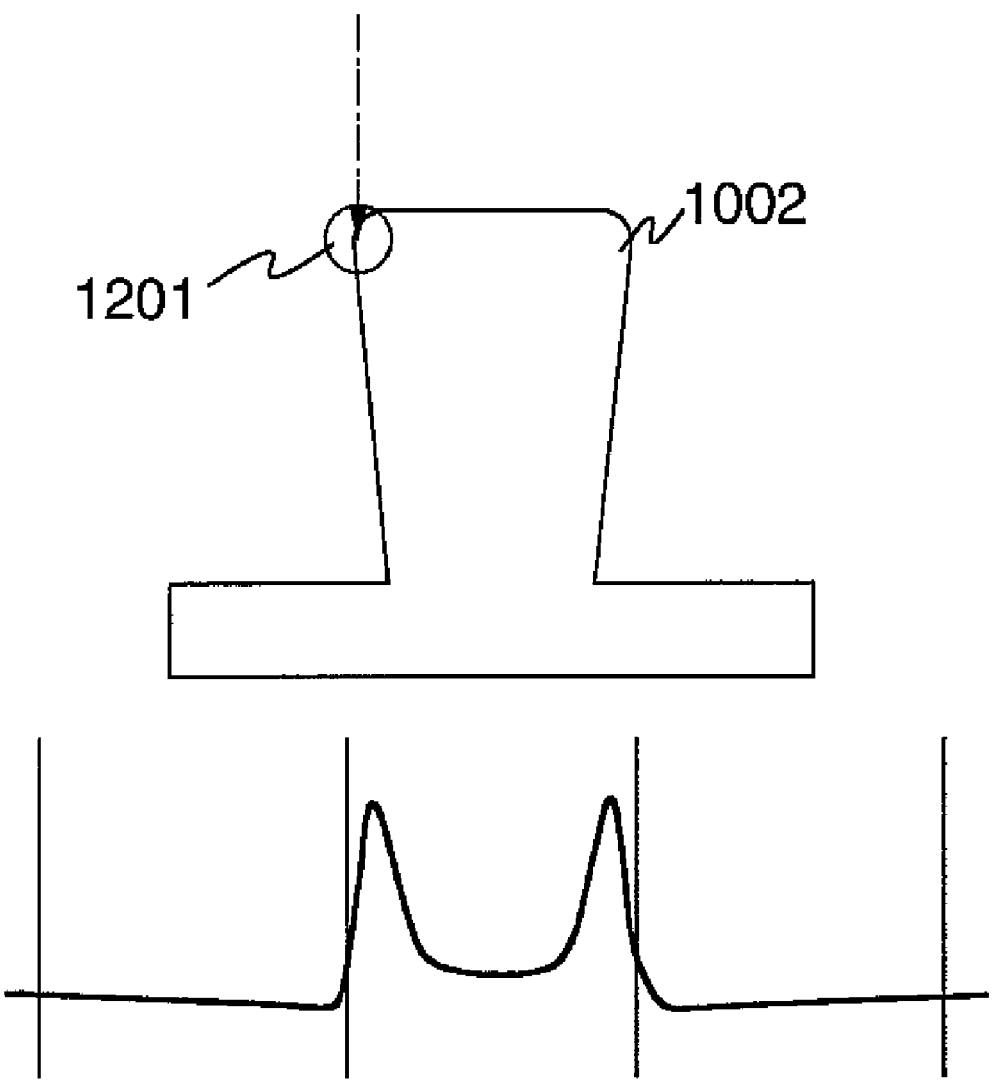

SAMPLE AND METHOD FOR EVALUATING RESOLUTION OF SCANNING ELECTRON MICROSCOPE, AND ELECTRON SCANNING MICROSCOPE

CROSS REFERENCE TO RELATED APPLICATION

This application is a continuation of U.S. application Ser. No. 11/779,899, filed Jul. 19, 2007, now U.S. Pat. No. 7,605,364 the contents of which are incorporated herein by reference.

INCORPORATION BY REFERENCE

The present application claims priority from Japanese application JP 2006-253718 filed on Sep. 20, 2006, the content of which is hereby incorporated by reference into this application.

BACKGROUND OF THE INVENTION

The present invention relates to an electron scanning microscope for carrying out dimensional measurement of a micro-pattern formed on a semiconductor substrate, a method of evaluating a resolution of a scanning electron microscope, and a sample for valuating a resolution of a scanning electron microscope, and in particular to a scanning electron microscope incorporating a function of evaluating a resolution of a scanning electron microscope from a picked-up image.

In a semiconductor manufacturing process, there have been demanded apparatuses for measuring dimensions with a higher degree of accuracy as the micro-patterns have been more and more fine. There has been known a scanning electro microscope for measuring a pattern width (a length measuring SEM (scanning electron microscope), or a CD (critical dimension) SEM), which are capable of picking up an image thereof with a magnification of one to five hundreds of thousands (100,000-500,000) as a dimension measuring tool for measurement of a micro-pattern having a size in the order of several ten nanometers.

The demands for measuring accuracy of these apparatuses include not only enhancing the measuring accuracy of the individual apparatus but also reducing differences among measured dimensions of several apparatuses installed on a production line and as well as reducing variations in measured dimensions which are caused by aging (or deteriorating with age) of the apparatus.

Of many factors for causing differences among measured dimensions of several apparatuses and for occurrence of variations in measured dimensions due to aging of the apparatuses, there may be exemplified differences and variation in resolution caused by differences among beam sizes and/or variation in the beam size due to aging. However, it is difficult to directly measure a size of an electron beam. Thus, in a scanning electron microscope, there has been used such a process that index values of resolution are measured from SEM images picked up by respective apparatuses, and differences among the beam sizes are evaluated by comparative evaluation of the index values.

As a specific example of a technique for measuring a resolution, U.S. Pat. No. 6,545,275 (Patent Document 1) and Metrics of resolution and performance for CD-SEMs by D. C. Joy et al, Metrology, Inspection, and Process Control for Microlithography XIV, page 108 (Nonpatent Document 1) propose, as examples thereof, a method in which an image is picked up from a sample prepared by depositing gold particles on a silicon substrate, and frequencies are analyzed through Fourier transformation of the picked-up image in order to calculate an index value of resolution. Further, U.S. Pat. No. 5,969,273 (Patent Document 2) and Modeling and Experimental Aspects of Apparatus Beam Width as an Edge Resolution Measure, C. Archie et al, Metrology, Inspection, and Process Control for Microlithography XIII, page 669 (Nonpatent document 2) propose such a technique that an image is picked up from a pattern formed on a substrate so as to measure a width corresponding to a pattern edge part in order to calculate an index value of resolution. Furthermore, JP-A-2005-268231 (Patent Document 3) and Contrast-to-gradient method for the evaluation of image resolution taking account of random noise in scanning electron microscopy, T. Ishitani et. al, J. Electron Microscopy 53(3) page 245 (Nonpatent Document 3) propose such a technique that a plurality of partial resolutions is obtained from respective partial zones in a picked-up image, and an average of partial resolutions over the entire image is calculated in order to calculate an index value of resolution.

In a scanning electron microscope apparatus for measuring dimensions of a pattern, a conventional resolution measuring process in which a picked-up image is used comprises the steps of (A-1) acquiring a picked-up image from a sample which is silicon substrate deposited thereon with gold or a porous silicon substrate, and (B-1) subjecting the picked-up image to Fast Fourier Transformation in order to analyze frequencies so as to calculate an index value of resolution. Further, another conventional resolution measuring process comprises the steps of (A-2) acquiring an image picked up from a pattern formed on a substrate, and (B-2) measuring a width corresponding to an edge part of the pattern from the picked-up image so as to calculate an index value of resolution.

A secondary electron image obtained by the scanning electron microscope, is in general exhibited by a convolution integration of a f(x, y) and g(s,t), where f(x,y) is a signal determined by a material of a sample and a pattern shape, and g(s,t) is a shape of an electron beam irradiated onto the sample. That is, in order to measure a size of an electron beam from a secondary electron image, it is required to take into consideration an influence caused by the signal f (x, y) which is determined by a sample and which is included in the image.

Estimating that the measurement of a resolution is carried out with the use of a dedicated sample, it is desirable for the sample to have one and the same pattern, one and the same pattern sectional shape and one and the same pattern distribution everywhere on the sample, even though it is not required to consider a variation in the signal due to a material quality. However, it is impossible to prepare such a sample, and the following problem will be caused.

Since the sample used in (A-1) has such a feature that analogous patterns each having a size of several ten nanometers are distributed in random over the entire surface of the sample, if an image having many patterns can be obtained, it is expected to calculate an index value of resolution with respect to an averaged value of the signals (x, y). However, if the distribution densities, the averaged sizes or pattern sizes of the analogous patterns, are uneven, or if the sectional shapes vary thereamong, the averaged value of the signals (x,y) will be of course, changed, and accordingly, the sample should be prepared by controlling these items in order to decrease the dependency upon the individual sample characteristics. Similarly, even with a pattern formed on a substrate used in (A-2), the signals f(x,y) are different from one another, and accordingly, the index value of resolution depends upon the individual sample characteristics.

Further, even with respect to a resolution evaluating algorithm, in the technique used in (B-1), if a pattern distribution on a sample becomes different, an index value of resolution obtained by calculation has a different characteristic and therefore dependency upon a pattern does not become small. In the technique used in (B-2), if a pattern roughness becomes different in an image zone used for calculation of a resolution, the index value of resolution will change, and accordingly, the pattern dependency is also not negligible.

In view of the above-mentioned matters regarding the resolution monitor, a resolution problem inevitably has such a task that the preparation of a sample and the utilization of a measurement algorithm, which are capable of reducing the pattern dependency of an index value of resolution to be measured are required for precisely measuring a variation in size of an electron beam.

SUMMARY OF THE INVENTION

An object of the present invention is to provide a sample for evaluation of a resolution of a scanning electron microscope, which is capable of stably evaluating a resolution with a high degree of sensitivity, a method of evaluating a resolution of a scanning electron microscope, and a scanning electron microscope.

According to the present invention, there is provided a sample with a pattern having a sectional shape which is appropriate for a resolution monitor. The shape appropriate for the resolution monitor is specifically such that a pattern on the sample has a side wall which is inclined so as to prevent an irradiated primary electron beam from impinging on the side wall. Accordingly, there can be provided a pattern monitor which is independent from a sectional shape of a pattern.

Further, according to the present invention, there is provided a resolution measuring method for evaluating a resolution with the use of an algorithm, by obtaining partial resolutions from partial zones in a picked-up image from the above-mentioned sample in order to calculate averaged partial resolution over the entire image so as to calculate an index value of resolution, as disclosed in the patent document 3. Thus, it is possible to provide a resolution monitor which can hardly be subjected to an affection caused by a pattern distribution, a pattern configuration and a sectional shape of a pattern.

Further, with the use of the above-mentioned method, according to the present invention, there is provided a scanning electron microscope capable of managing a resolution.

That is, according to the present invention, a sample for evaluating unevenness in resolution among several scanning electron microscopes or a sample for evaluating an aging in resolution of a designated scanning electron microscope is characterized in that a concave and convex pattern is formed on its outer surface, having a backward tapered sectional shape such as to have an upper part and a lower part which is narrower than the upper part.

Further, according to the present invention, a sample for evaluating unevenness in resolution among several scanning electron microscopes or a sample for evaluating an aging in resolution of a designated scanning electron microscope is characterized in that a concave and convex pattern is formed on its outer surface, the concave and convex pattern being formed so that a side wall surface part on the concave and convex pattern falls in a shadow of the upper surface of the concave and convex pattern with respect to an electron beam perpendicularly incident upon the sample.

Further, according to the present invention, there is provided a method for evaluating a resolution of a scanning electron microscope, characterized in that an image of the above-mentioned sample for evaluating a resolution of a scanning electron microscope is picked up successively by several scanning electron microscopes, and respective images picked up by these several scanning electron microscopes are processed in order to evaluate unevenness in resolution among the several scanning electron microscopes.

Further, according to the present invention, there is provided a method for evaluating a scanning electron microscope, characterized in that image of the above-mentioned sample for evaluating a resolution of a scanning electron microscope is picked up, and image picked up is compared with data which has been stored in a storage means so as to evaluate an aging of resolution of the scanning electron microscope.

Further, according to the present invention, there is provided a scanning electron microscope characterized in that the above-mentioned sample for evaluating a resolution is installed therein.

Further, according to the present invention, there is provided a scanning electron microscope characterized by a function for correcting an image obtained by observing a sample to be observed or data obtained by processing the image, in accordance with a result of evaluation of a resolution with the use of the above-mentioned sample for evaluating a resolution.

According to the present invention, the scanning electron microscope with the use of a sample for evaluating a resolution can measure a resolution with a higher degree of accuracy, and as a result, a variation in resolution of a scanning electron microscope and differences in resolution among scanning electron microscopes can be managed with a high degree of accuracy. Thus, it is possible to measures dimensions with a higher degree of reliability and a high degree of accuracy during, for example, a process of manufacturing a semiconductor pattern, resulting in an improvement in performance of a product and in an improvement in the yield thereof.

These and other objects, features and advantages of the invention will be apparent from the following more particular description of preferred embodiments of the invention, as illustrated in the accompanying drawings.

BRIEF DESCRIPTION OF THE DRAWINGS

FIG. 12 is a view illustrating a sectional shape of a sample for evaluating a resolution, and an SEM image thereof and a secondary electron signal waveform which are superposed with each other.

DESCRIPTION OF THE PREFERRED EMBODIMENTS

Explanation will be hereinbelow made of an embodiment of the present invention with reference to the accompanying drawings.

In this embodiment, an image of a sample for evaluating a resolution, which has been obtained by a scanning electron microscope, is evaluated in order to evaluate and manage a resolution of the above microscope.

(0) Sequence

Figure 1:
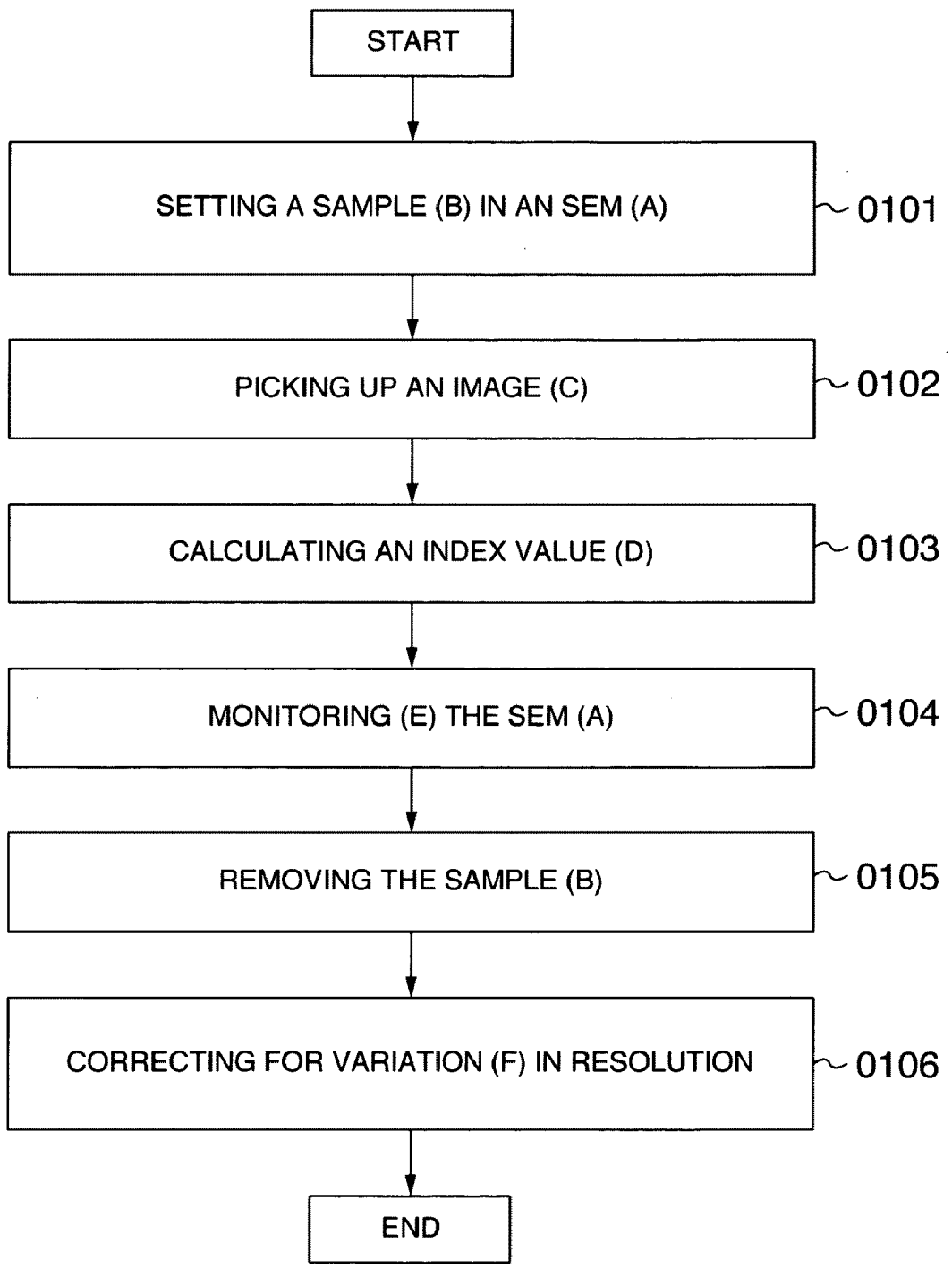
FIG. 1 is a view illustrating a sequence for evaluating a resolution, according to the present invention.

Referring to FIG. 1 which shows a sequence for evaluating a resolution, according to the present invention, the sequence comprises, at first, a step 0101 of setting a sample (B) for evaluating a resolution, onto a scanning electron microscope (A) whose resolution is to be evaluated, a step 0102 of picking up an image (C) of the sample (B) for evaluating a resolution, a step 0103 of calculating an index value (D) of resolution of the microscope from the picked-up image (C), a step 0104 of then storing the thus calculated index value (D) of resolution for each microscope and for each time series in order to monitor a condition of the scanning electron microscope, a step 0105 of removing the sample (B) for evaluating a resolution from the scanning electron microscope (A), and a step 0106 of correcting the scanning electron microscope (A) and the picked-up image (C) for a variation (F) in resolution in accordance with a result of the monitor of the condition of the scanning electron microscope which monitor was carried out at the step 0104 if the index value (D) of resolution becomes out of a preset range.

The sample (B) for evaluating a resolution, which is set at the step 0101, may be beforehand set on the scanning electron microscope (A). Alternatively, the sample (B) for evaluating a resolution, may have been beforehand held at a predetermined position in or outside of the scanning electron microscope (A), and may be automatically set in the scanning electron microscope (A).

Next, explanation will be hereinbelow made of the respective steps of the above-mentioned sequence in detail.

(A) Scanning Electron Microscope

Figure 2:
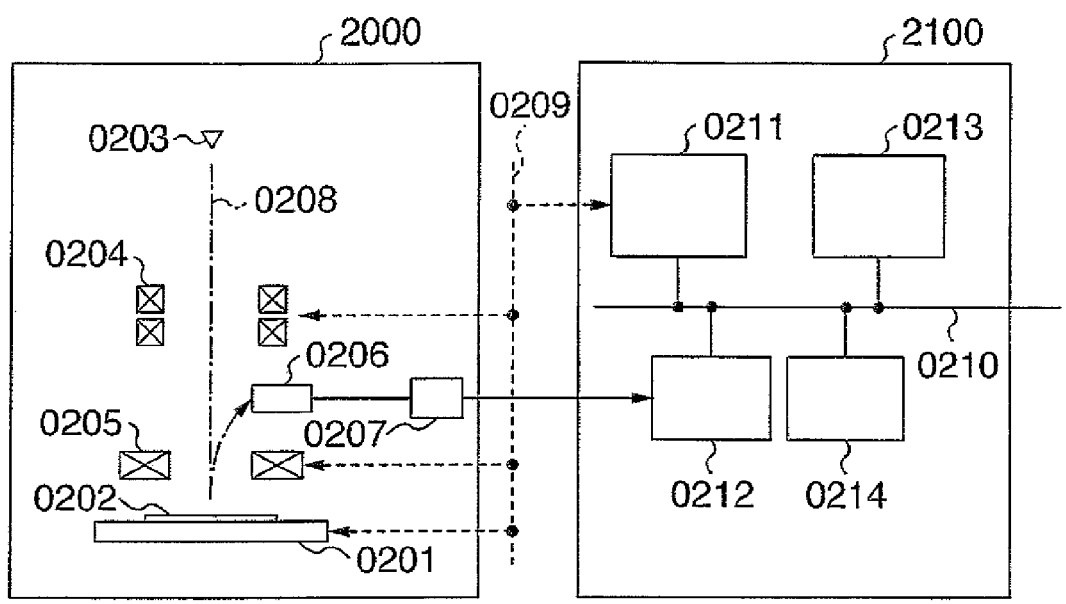
FIG. 2 is a schematic view illustrating a configuration of a system incorporating a scanning electron microscope.

Referring to FIG. 2 which shows a configuration of a scanning electron microscope (A) for measuring dimensions, according to the present invention, the scanning electron microscope is mainly composed of two portions, that is, an electron optical system 2000 for picking up or obtaining electron beam images, and a data processing system 2100 for processing the obtained images so as to measure an objective pattern.

The electron optical system 2000 is mainly composed of a stage 0201 for carrying thereon a sample 0202, an electron source 0203 for emitting an electron beam 0208, a deflection lens 0204 for deflecting the electron beam 0208, an objective lens 0205 adapted to be controlled in order to pick up an image at a position of a focused point, a secondary electron detector 0206 having a function of converting secondary electrons produced from a sample, into an electric signal, an A/D converter 0207 for converting the detected electric signal into a digital signal, and a control portion 0211 for controlling the above-mentioned components.

Meanwhile, the data processing system 2100 for measuring a picked-up pattern from image data is mainly composed of a process portion 0213 for processing an image and so forth, a storage portion 0212 for storing image data and various data adapted to be used for other processes, and an input/output portion 0214 having a function of allowing the user to input an image pick-up condition and parameters for the image process, the input/output portion 0214 also having a function of outputting an obtained result, among which portions data is delivered and received to and from one another through a data bus 0210. Further, the control portion 0211 shown in the figure, is adapted to carry out not only the control for the electron optical system but also control for measuring dimensions of a pattern from a picked-up image (the control portion 0211 is shown within the data processing system 2100 in the case of the configuration of the scanning electron microscope (A) according to the present invention, as shown in FIG. 2).

Figure 3:
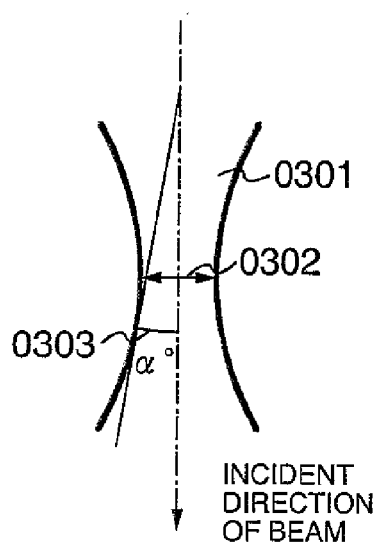
FIG. 3 is a view illustrating an electron beam which is in a state of being converged.
Figure 4A:
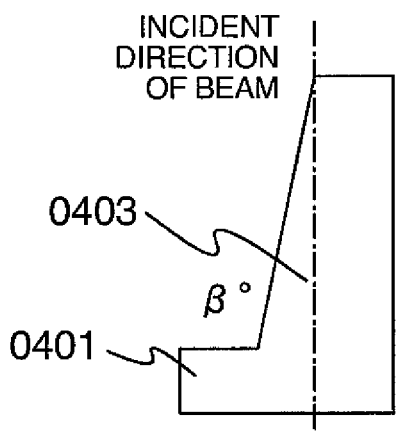
FIG. 4A is a view illustrating a sectional shape of a pattern on a sample.
Figure 4B:
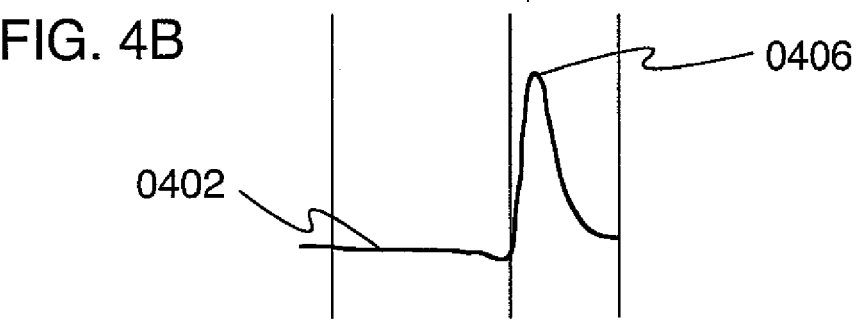
FIG. 4B is a view illustrating an SEM image detected by irradiation of an electron beam onto a pattern and a secondary electron signal waveform, which are superposed with each other.
Figure 4C:
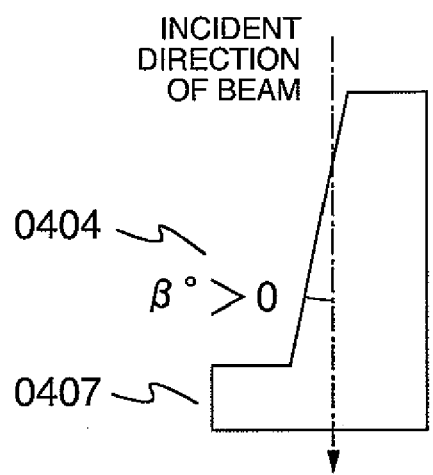
FIG. 4C is a view illustrating a relationship between a pattern having a forward tapered sectional shape, and an incident direction of an electron beam.
Figure 4D:
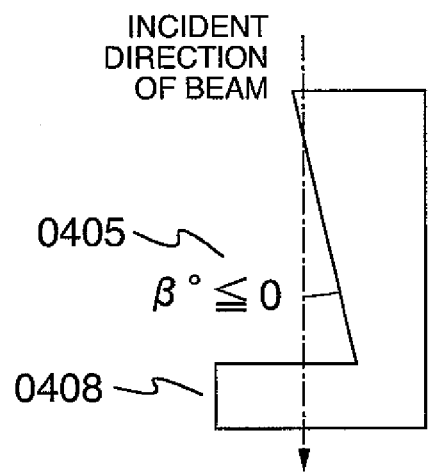
FIG. 4D is a view illustrating a relationship between a pattern having a backward tapered sectional shape and an incident direction of an electron beam.

This embodiment has a purpose of monitoring a variation in the shape of an electron beam, caused by an individual difference of the electron optical system, an aging and the like. Referring to FIG. 3 which shows a schematic view 0301 of a shape of an electron beam, the beam is diverged by a diverging angle α (0303) both forward and rearward of the incident direction of the electron beam, from a position where the beam is converged to the fullest, that is, a beam waist position 0302 as a mid point. It is assumed in this embodiment that the diverging angle α is not greater than about 1 degree.

(B) Sample

In this embodiment, a secondary electron signal image obtained by scanning the sample for evaluating a resolution by the above-mentioned electron beam over is analyzed in order to calculate an index value of resolution. The secondary electron signal image is the one which is an image of intensities of secondary electron signals emitted from the sample through the irradiation of a scanning electron beam over the sample. The secondary electron signals are in general represented by a convolution integral of two functions f and g, where f is a signal f(x,y) determined by a configuration and a material quality of a pattern on the sample, and g is an electron beam g(s,t).

Referring to FIGS. 4A to 4D which schematically show the respective relationships between various sectional shapes of a pattern and a secondary electron signal, the intensity f of the secondary electron signal 0402 emitted from the pattern 0401 depends upon a relative angle β between the incident direction of the beam and the side wall of the pattern. The relative angle β 0403 is set to be positive 0404 in such a case that the electron beam is directly irradiated upon the side wall of the pattern, but to be negative 0405 in such a case that it is not directly irradiated upon the side wall. The relative angle β can be taken in an angle range from −90 to +90 deg., and it conceived that the following relationship (Formula 1) is satisfied in a range in which the relative angle β is greater than 0 deg. but not greater than 90 deg:

$$f \propto 1/\cos(\beta)$$ Formula 1

Further, as understood from the above-mentioned relationship (Formula 1), a secondary electron signal having a relatively high intensity 0406 is emitted from the edge part of the pattern due to the so-called edge effect.

In view of the above-mentioned principles, the intensities of the secondary electron signals are schematically shown in FIGS. 5A to 5E, with respect to various sectional shapes. The pattern on the sample has a top surface and a bottom surface. Assuming that both of the surfaces cross the incident direction of the electron beam, at a substantially right angle thereto, in such a case that the electron beam incident perpendicular to the sample is not made into contact with the side wall of the pattern, as denoted by 0501 and 0503 shown in FIGS. 5A and 5B, that is, the relative angle β between the incident direction (vertical direction) of the electron beam and the side wall of the pattern is not greater than 0 deg. (the width thereof is larger in the upper part (on the outer surface side) than in the lower part (on the base side) of the pattern in its sectional shape, that is, the sectional shape of the pattern is backward tapered), the signal f obtained by detecting the secondary electrons has a waveform which is enhanced only in its edge effect, as indicated by 0502 and 0504 shown in FIGS. 5A and 5B, that is, which does not depend upon the relative angle β.

Figure 5A:
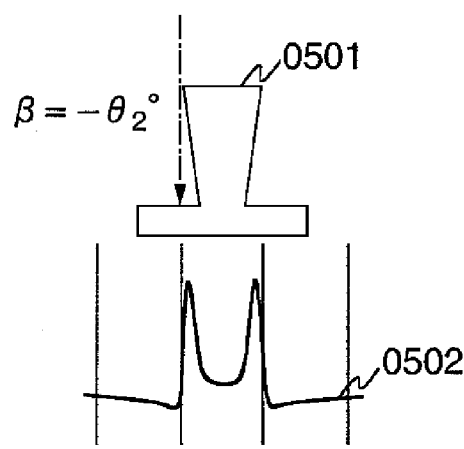
FIG. 5A is a view illustrating a relationship between a pattern having a backward tapered sectional shape, and an incident direction of an electron beam, the tapered angle being large.
Figure 5B:
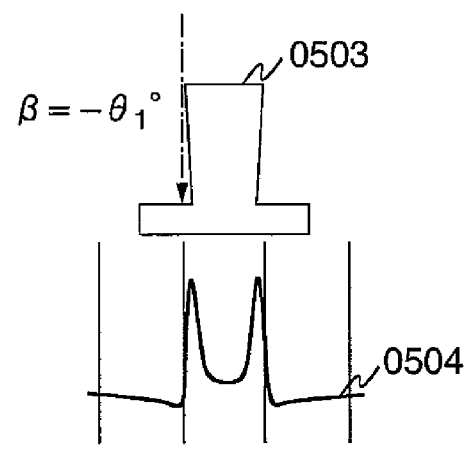
FIG. 5B is a view illustrating a relationship between a pattern having a backward tapered sectional shape, and an incident direction of an electron beam, the tapered angle being small.
Figure 5C:
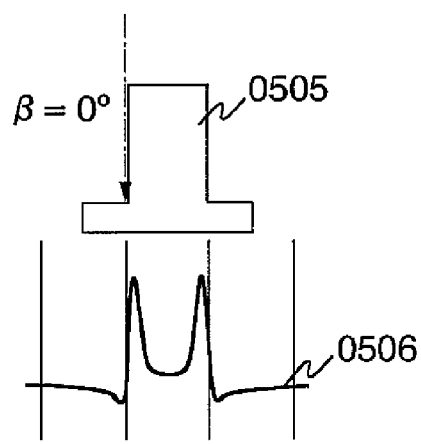
FIG. 5C is a view illustrating a relationship between a pattern having a substantially vertical sectional shape, and an incident direction of an electron beam.
Figure 5D:
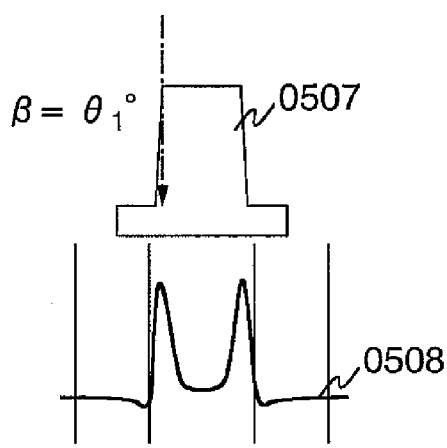
FIG. 5D is a view illustrating a relationship between a pattern having a forward tapered sectional shape, and an incident direction of an electron beam, the tapered angle being small.
Figure 5E:
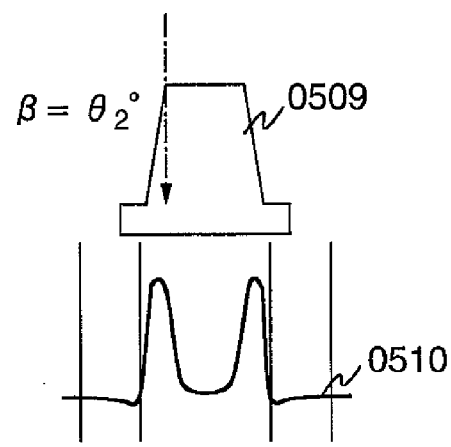
FIG. 5E is a view illustrating a relationship between a pattern having a forward tapered sectional shape, and an incident direction of an electron beam, the tapered angle being large.

On the contrary, it can be understood that the secondary electron signal f is changed as indicated by 0508 in FIGS. 5D and 0510 in FIG. 5E, when the inclined angle of the side wall of the pattern varies so as to change the relative angle β between the side wall of the pattern and the incident direction of the electron beam, in view of the above-mentioned formula 0406 in such a case that the electron beam which is incident upon the sample, perpendicular thereto, is irradiated upon the side wall of the pattern, as indicated by 0507 in FIGS. 5D and 0509 in FIG. 5E, (the width is greater in the lower part than in the upper part of the pattern in its sectional shape, that is, the pattern has a forward tapered sectional shape), that is, the relative angle β between the incident direction (vertical direction) of the electron beam and the side wall of the pattern is positive.

As stated above, since the image of the secondary electron signal is changed not only by the shape of the electron beam but also by the sectional shape of the pattern, there is raised such a task that variation in an index value of resolution in dependence upon a sectional shape of a pattern should be decreased whenever an index value of resolution is calculated from the picked-up image.

By the way, it is extremely difficult to practically form a pattern having one and the same sectional shape everywhere on the sample. Accordingly, on the basis of the result shown in FIGS. 5A to 5D, there will be taken, for a sample producing a secondary electron image which can hardly be changed even though the sectional shape of the pattern on the sample is uneven, a sectional shape having such a side wall angle that the electron beam is prevented from irradiating upon the side wall of the pattern as possible as it can, that is, the relative angle β between the incident direction of the electron beam and the side wall of the pattern is not greater than 0 deg., as indicated by 0501 in FIGS. 5A and 0503 in FIG. 5B. Thus, with such a sectional shape that the top surface of the sample casts a shadow on the side wall surface thereof with respect to the electron beam which is incident upon the top surface of the sample, perpendicular thereto. By this sectional shape, the electron beam incident upon the sample will be prevented from being incident directly upon the side wall surface of the sample, thereby it is possible to detect a secondary electron signal which excludes any data concerning the side wall surface.

Figure 6:
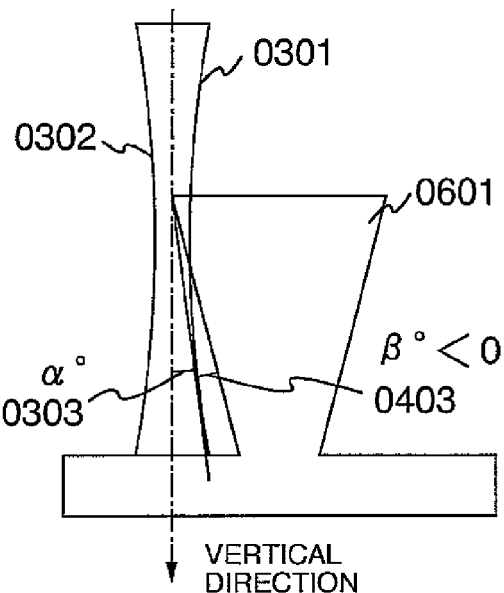
FIG. 6 is a view illustrating a relationship between a sectional shape of a pattern on a sample for evaluating a resolution, and a sectional shape of an incident electron beam.

Actually, the incident direction of the electron beam is inclined to the vertical direction or has a diverging angle as shown in FIG. 3, and accordingly, it is required to select a side wall angle of the pattern in view of this matter. For example, as shown in FIG. 6, if the beam waist 0302 of the electron beam 0301 which is incident upon the sample in the vertical direction is adjusted to a position in the vicinity of the top surface of the pattern 0601, a diverging angle α is produced in the part forward from the beam waist 0302 (said part is on the base side of the pattern 0601). Accordingly, in order to accurately evaluate a resolution with the use of the electron beam having such a diverging angle α, it had better to use a sample having a side wall which is inclined inward by an angle of not less than α with respect to the vertical direction.

With the above-mentioned condition being satisfied, the unevenness of the secondary electron signals thus obtained can be reduced even though the sectional shapes of the pattern is uneven, thereby it is possible to calculate the index value of resolution with the reduced affection by the sectional shape of the pattern.

Figure 7:
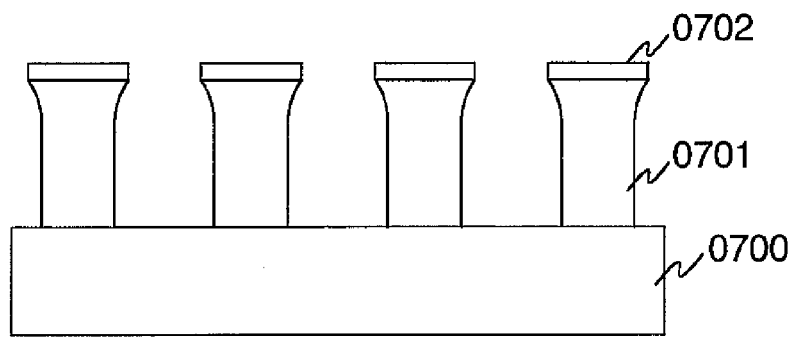
FIG. 7 is a view illustrating a sectional shape of a sample for evaluating a resolution, as an example.

As a sample which can satisfy the above-mentioned condition, there may be used, for example, a sample having an etching pattern which depicts lines, trenches, dots, holes or the like which has an arbitrary shape. FIG. 7 shows an example of a process for forming a sample having a side wall inclined inward of a pattern as shown in FIG. 6. That is, in a process before a manufacture of a semiconductor, a film 0701 made of a material having a high etching rate is formed on an Si substrate 0700 and a thin film 0702 made of a material having a low etching rate and having a thickness of about 10 nm is formed thereon. Next, a resist (which is not shown) is applied over the thus laminated film, and then, a pattern is exposed thereon, and developed. Then, the thus obtained resist pattern (which is not shown) is used as a mask for etching in order to form a pattern as shown in FIG. 7. Due to different etching rates, the lower film 0701 is greatly etched, and accordingly, a sample having a side wall inclined inward of the pattern can be provided.

Figure 10:
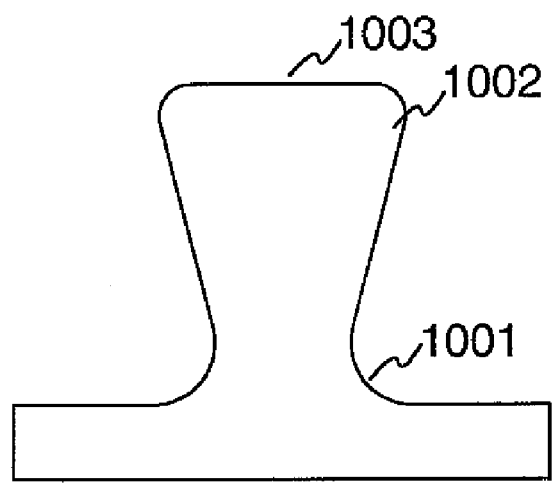
FIG. 10 is a schematic view illustrating a sectional shape of a pattern in general.
Figure 11:
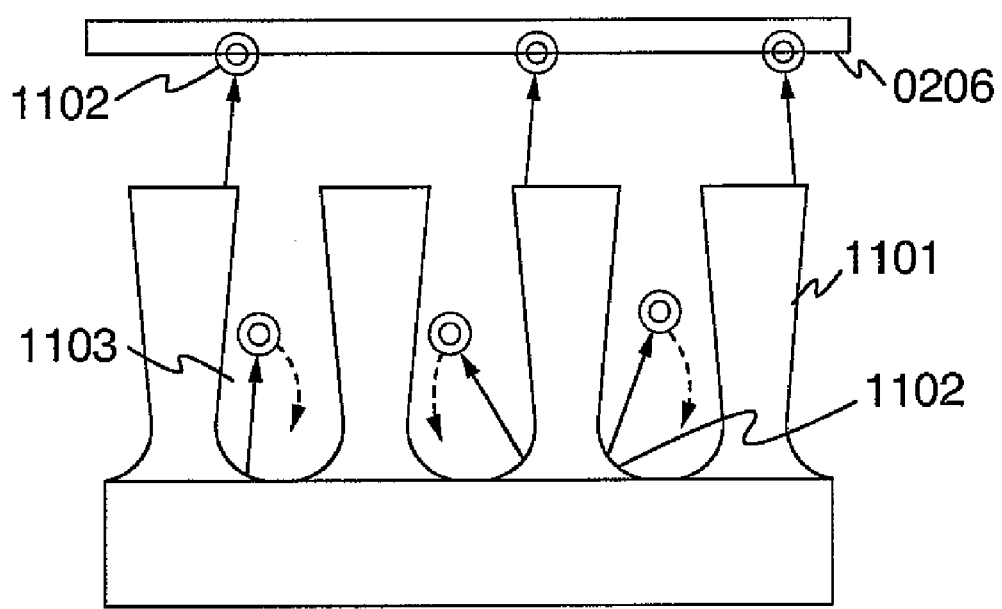
FIG. 11 is a view schematically illustrating sectional shapes of a sample having a sufficiently large height, for evaluating a resolution and a detector.

As an indicator of a pattern sectional shape, in addition to the inclined angle of the side wall, there may be exemplified a corner rounding (fitting) 1001 of a lower part of the pattern and a corner rounding (top rounding) of the upper part of the pattern, as shown in FIG. 10. If the fitting 1001 is present, the secondary electron signal is changed, depending upon a shape of the fitting, and accordingly, it is desirable that the fitting 1001 is as small as possible. Alternatively, as shown in FIG. 11, if the sample has such a sectional shape that the height of the pattern 1101 is sufficiently high, and accordingly, the secondary electrons 1103 emitted from the fitting part 1102 cannot reach a secondary electron detector 206, no affection by the fitting 1102 is exhibited in the secondary electron image, thereby it is possible to reduce the shape dependency of the sample.

The secondary electron signal is also changed in dependence upon a shape of the top rounding 1002 shown in FIG. 10, and accordingly, it is desirable that the top rounding 1062 is small as possible and the top surface of the pattern is flat. However, as shown in FIG. 12, since the intensity of the secondary electron beam is strong in the part where the top rounding 1002 is produced, due to the above-mentioned edge effect, and can be hardly subjected to affection by a shape change in comparison with secondary electrons produced from the fitting 1001 or the fitting 1102. In particular, it may considered that a zone where a secondary electron signal having a strong intensity can be obtained due the edge effect, is substantially coincide with an electron scattering area 1201 in a pattern around the top of the edge as a center, and accordingly, even though the top rounding 1002 is present in this zone, it may be considered that the secondary electron signal cannot be easily changed.

Thus, if the electron scattering zone in the pattern has a circular shape having a radius R, it is desirable that the top rounding is smaller than an arc having the radius R. The electron scattering zone in the pattern varies, depending upon a material quality of the sample, optical conditions (an acceleration voltage, a probe current and the like) of the electron beam and the like, within a range of radius from several nanometers to several ten nanometers.

C. Image Pick-Up

In order to evaluate a resolution with the use of the sample as mentioned above, with several repetitions, for one and the same zone, of such a process that a desired zone on the sample is scanned by the electron beam so as to obtain a secondary electron detection signal for one frame in order to obtain a second electron detection signals for several frames, the secondary electron signals for the several frames are added together (addition of frames) so as to obtain an image for evaluating a resolution. Since the detectability is high in the case of a condition that the size of one pixel being smaller than the size of the electron beam, it is desirable to pick up an image with a magnification which can satisfy the above-mentioned condition in order to detect a variation in the size of the electron beam.

Although errors during measurement of a resolution caused by unevenness of sectional shapes of patterns, can be decreased to a certain degree with the use of the above-mentioned sample, there would be still remained affections by unevenness in pattern shape, pattern sectional shape and pattern distribution, and accordingly, in order to reduce such affections, index values of resolution are calculated N number of images, which have been obtained at N number of places on one and the same sample, and then, the evaluation of resolution is carried out by using an averaged value of the thus obtained index values of resolution. The required number N of picked-up images varies depending upon a required degree of accuracy for measuring a resolution. As an example, there may be used such a technique that the number N of picked-up images is selected so that a value which is obtained by dividing a degree V of unevenness in measurement for index values of resolution on a sample to be used, with a square root of N, is smaller than a required degree S. This technique has been known as a center limit theorem.

Figure 8:
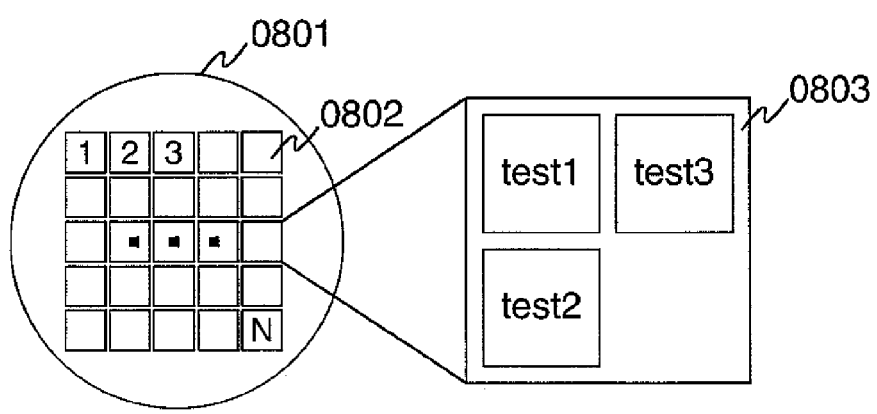
FIG. 8 is a view illustrating a procedure for obtaining an image for measuring a resolution(D), as an example.

The manner for determining a zone from which images at N places are picked up from a sample, may be random. Alternatively, as shown in FIG. 8, the N places at which images are picked up from a sample 0801 can be taken as denoted by reference numeral 0803 in which they are adjacent to one another for each evaluation of resolution, thereby it is possible to compare results of evaluation of resolution in adjacent patterns on the sample with each other. With the comparison between the adjacent patterns, even though a biased distribution of pattern shapes or sectional shapes is present within the sample, the measurements of resolution can be stably carried out without being affected by such biased distribution.

D. Algorithm for Calculating an Index Value of Resolution

Explanation will be hereinbelow made of an algorithm for calculating an index value of resolution from images for evaluating a resolution, which are picked up as stated above. As to the resolution calculating algorithm, there may be in general known several techniques, as exemplified in Non-patent Documents 1 to 3, and any of these techniques may be used. However, in this embodiment, a CG (Contrast to Gradient) process is used. The CG process utilizes such a technique that index values of local resolution are calculated from local zones in an image, and a weighted average of index values of local resolution is obtained over the entire image as an index value of resolution. In this technique, since the index values are calculated from local zones at the first step, it is possible to decrease measurement errors for resolution caused by different pattern shapes and different pattern distributions on the sample.

As stated above in the item C: Image Pick-Up, index values of resolution for N number of images are obtained, and an average thereof is then obtained as an index value of resolution for a scanning electron microscope to be evaluated, thereby it is possible to measure a resolution with less affection by a pattern.

E: Monitor of Condition of Electron Microscope

Figure 9:
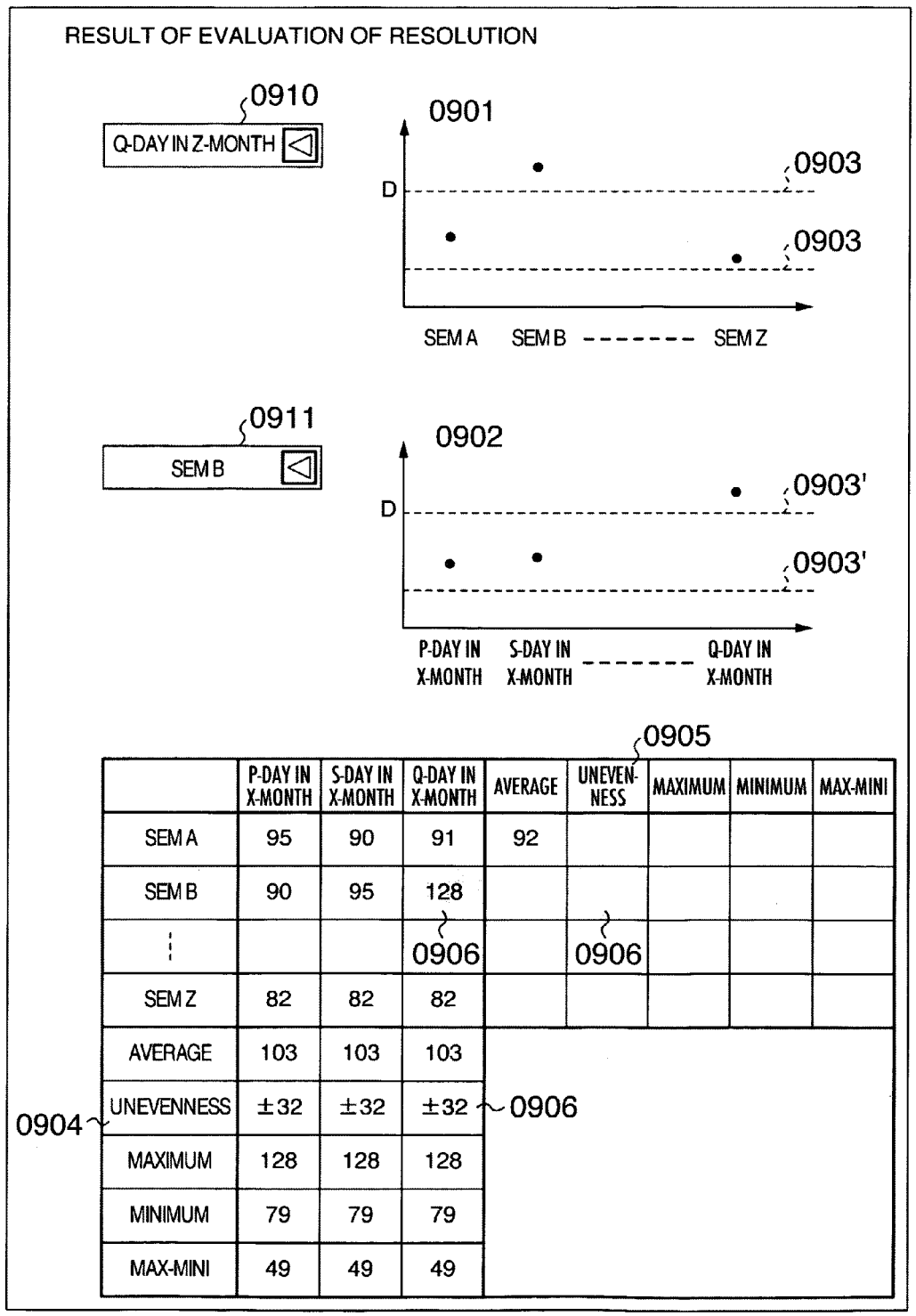
FIG. 9 is a view illustrating an output screen for a result of evaluation of a resolution(D), as an example.

Referring to FIG. 9 which shows an example of a GUI of a system for monitoring a condition of the electron microscope with the use of calculated index values of resolution, the GUI includes a portion 0901 for comparing and displaying index values of resolution among electron microscopes, which have been measured on a day or during a period which is designated by a selection button 0910 on a screen, and a portion 0902 for displaying an aging of an index value of resolution for a single electron microscope designated by a designation button 0911 on the screen. Further, if each index value becomes out of a preset range 0903 or 0903', or if a degree 0904 of unevenness in index value of resolution among electron microscopes or an aging 0905 becomes greater than a preset value, it is possible to issue an alarm for warning 0906.

By monitoring a condition of the electron microscope with the use of the index values of resolution, the performance of the monitored electron microscope can be ensured, thereby it is possible to obtain a result of dimensional measurement with a high degree of reliability.

F. Correction

Finally, explanation will be made of a function of correcting electron microscopes, images or pattern dimensions measured from the images on the basis of the thus obtained index values of resolution.

In order to correct the electron microscope, there may be used such a method that adjustment for microscope parameters and measurement of an index value of resolution are repeated until the index value of resolution becomes a desired value. As the microscope parameters, there may be exemplified an acceleration voltage, a parameter for adjusting aberration of an electron beam, a focus parameter, a parameter for adjusting an electromagnetic lens and the like. In addition, it is possible to adjust a parameter on the basis of data as to a relationship between a parameter adjusting value for adjusting a resolution and an index value of resolution which relationship has been previously checked. These adjustments are carried out by the control portion 0211 shown in FIG. 2.

In order to correct the image, there may be exemplified a method for using an image filter in order to set the index value of resolution to a desired value. As the above-mentioned image filter, a Gaussian function type filter having a shape similar to that of the electron beam may be used. The index value of such a filter is adjusted based upon the index value of resolution, and with the use of the thus adjusted filter, images are processed for convolution, deconvolution or the like, thereby it is possible to reform the images picked up by plurality of electron microscopes having various index values of resolution, into images which are as those picked up the electron microscopes having the same index value of resolution. By measuring pattern dimensions from these images, unevenness of measured dimensions caused by different resolutions can be reduced. This correction is carried out by the processing portion 0213 shown in FIG. 2.

In the case of direct correction for pattern dimensions measured from images, there may be exemplified a method for adding offsets to measured dimensions. That is, the relationship between an index value of resolution and a result of measurement of dimensions of a typical pattern have been beforehand checked, and differences between measured dimensions having a target index value of resolution and those having a practical index value of resolution are used as offsets, thereby it is possible to reduce differences in the measured dimensions caused by differences in resolution. These corrections is carried out by the processing portion 0213 in FIG. 2.

Further, the correction may also be made in the combination of the correction for an electron microscope, the correction for the image, and the direct correction for pattern dimensions measured from images, each correction procedure is above-mentioned respectively.

The evaluation of resolution of a scanning electron microscope and the correction therefor can be made through the sequence shown in FIG. 1, as stated above. Thus, dimensional data of a pattern, which is individually measured by a plurality of scanning electron microscopes, can be compared with one another with a relatively high degree of reliability. Further; it is possible to maintain a uniform degree of reliability for the resolution of a scanning electron microscope over a long time.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A method of evaluating a resolution of a scanning electron microscope, comprising the steps of:
   picking up a first image of a concave and convex pattern formed on a surface of a sample utilizing a first scanning electron microscope;
   picking up a second image of the concave and convex pattern on the sample utilizing a second scanning electron microscope;
   respectively processing the first image and the second image in order to evaluate unevenness in resolution between the first scanning electron microscope and the second scanning electron microscope; and
   determining whether a height of the concave and convex pattern as measured from a bottom thereof is sufficient so that no affection by a secondary electron emitted from the bottom of the concave and convex pattern is exhibited.

2. A method of evaluating a resolution of a scanning electron microscope according to claim 1, wherein the concave and convex pattern has a rounded portion where a concave part and a convex part of the concave and convex pattern join.

3. A method of evaluating a resolution of a scanning electron microscope according to claim 1, wherein the first image and the second image of the concave and convex pattern are those which do not substantially include data as to a side wall of the concave and convex pattern.

4. A method of evaluating a resolution of a scanning electron microscope as set forth in claim 1, wherein the first image obtained by picking up the concave and convex pattern with the use of the first scanning electron microscope and the second image obtained by picking up the concave and convex pattern with the used of the second scanning electron microscope, are each obtained by irradiating and scanning an electron beam which is converged so as to have a beam diverging angle smaller than an inclined angle of a side surface of the concave and convex pattern, in the vicinity of a beam waist thereof.

5. A method of evaluating a resolution of a scanning electron microscope as set forth in claim 1, wherein the concave and convex pattern has a backward tapered sectional shape.

6. A method of evaluating a resolution of a scanning electron microscope, comprising the steps of:
   picking up a first image of a concave and convex pattern formed on a surface of a sample utilizing a first scanning electron microscope;
   picking up a second image of the concave and convex pattern on the sample with the use of a second scanning electron microscope;
   respectively processing the first image and the second image in order to evaluate unevenness in resolution between the first scanning electron microscope and the second scanning electron microscope; and
   determining whether a top of the concave and convex pattern measured from a bottom thereof is enough high so that a secondary electron emitted from the bottom of the concave and convex pattern cannot reach a first secondary electron detector of the first scanning electron microscope or a second secondary electron detector of the second scanning electron microscope.

7. A method of evaluating a resolution of a scanning electron microscope according to claim 6, wherein the concave and convex pattern has a rounded portion where a concave part and a convex part of the concave and convex pattern join.

8. A method of evaluating a resolution of a scanning electron microscope according to claim 6, wherein the first image and the second image of the concave and convex pattern are those which do not substantially include data as to a side wall of the concave and convex pattern.

9. A method of evaluating a resolution of a scanning electron microscope as set forth in claim 6, wherein the first image obtained by picking up the concave and convex pattern with the use of the first scanning electron microscope and the second image obtained by picking up the concave and convex pattern with the used of the second scanning electron microscope, are each obtained by irradiating and scanning an electron beam which is converged so as to have a beam diverging angle smaller than an inclined angle of a side surface of the concave and convex pattern, in the vicinity of a beam waist thereof.

10. A method of evaluating a resolution of a scanning electron microscope as set forth in claim 6, wherein the concave and convex pattern has a backward tapered sectional shape.

* * * * *